United States Patent [19]  [11]  4,147,661
Higgins et al.  [45]  Apr. 3, 1979

[54] PRODUCTION OF MALEIC ANHYDRIDE AND CATALYSTS THEREFOR

[75] Inventors: Raymond Higgins; Graham J. Hutchings, both of Middlesbrough, England

[73] Assignee: Imperial Chemical Industries Limited, London, England

[21] Appl. No.: 848,719

[22] Filed: Nov. 4, 1977

[30] Foreign Application Priority Data

Nov. 11, 1976 [GB] United Kingdom ............... 46966/76

[51] Int. Cl.² ..................... B01J 27/14; C07D 307/60
[52] U.S. Cl. .................................. 252/435; 252/437; 260/346.75
[58] Field of Search ............................... 252/435, 437

[56] References Cited

U.S. PATENT DOCUMENTS

| 3,864,280 | 2/1975 | Schneider | 252/435 |
| 3,888,886 | 6/1975 | Joung | 252/435 X |
| 4,008,179 | 2/1977 | Gasson et al. | 252/437 |
| 4,045,478 | 8/1977 | Umemura et al. | 252/435 X |
| 4,052,417 | 10/1977 | Sunkard et al. | 252/437 X |
| 4,065,468 | 12/1977 | Grasselli et al. | 252/435 X |
| 4,070,379 | 1/1978 | Ciquier et al. | 252/435 X |
| 4,070,397 | 1/1978 | White et al. | 252/437 X |

FOREIGN PATENT DOCUMENTS

| 1425301 | 12/1964 | France | 252/435 |
| 1470581 | 12/1966 | France | 252/435 |

Primary Examiner—Delbert E. Gantz
Assistant Examiner—William G. Wright
Attorney, Agent, or Firm—Cushman, Darby & Cushman

[57] ABSTRACT

Catalysts for the oxidation of hydrocarbons to maleic anhydride comprise a phosphorus/vanadium mixed oxide promoted by tungsten antimony, niobium, and/or molybdenum, having a surface area of at least $10 m^2/g$.

6 Claims, No Drawings

PRODUCTION OF MALEIC ANHYDRIDE AND CATALYSTS THEREFOR

THIS INVENTION relates to the production of maleic anhydride and catalysts therefor.

It is known to produce maleic anhydride by oxidising hydrocarbons, for example those having the formula $R'$—$CH_2$—$CH_2$—$CH_2$—$CH_2R''$ where $R'$ and $R''$ are individually hydrogen or alkyl groups, $R'$ and $R''$ having together at most six and preferably at most four carbon atoms, or cyclo-alkanes having a —CH—CH$_2$—CH$_2$—CH— group, preferably in a ring, for example cyclohexane. Mixtures of hydrocarbons, for example naphtha, may be used but n-butane is a preferred feedstock. The hydrocarbon is generally oxidised by contacting it in the vapour phase together with oxygen with a solid catalyst and recovering maleic anhydride from the product. Oxygen may be provided in the form of air by mixing the hydrocarbon in a concentration generally, except in the case of fluidised bed processes, lower than the lower explosive limit and contacting the mixture with the catalyst under appropriate conditions of temperature and pressure (the "fuel lean" system). In this case the product gas, after recovery of maleic anhydride, is usually vented or burned. The oxidation may also be carried out for example by mixing the hydrocarbon in a concentration higher than the upper explosive limit with oxygen, contacting it with a catalyst under appropriate conditions of temperature and pressure, recovering maleic anhydride from the product gas and preferably recycling the remainder of the product gas to the reaction (the "fuel rich" system). It is possible to operate within the explosive limits using a fluidised bed reactor.

It is important that the catalyst should have a high selectivity, that is that the yield of maleic anhdyride should be as high as possible based on the hydrocarbon consumed in the process. In processes in which the product gas after recovery of maleic anhydride is vented or burned it is important therefore, that the pass yield should be high, ie. that the proportion of the hydrocarbon converted to maleic anhydride on a single pass should be as high as possible. In processes in which unconverted hydrocarbon is recycled it is desirable that a high pass yield should be achieved in order to avoid recycling an unduly high proportion of the hydrocarbon but the selectivity in terms of the yield of maleic anhydride based on the hydrocarbon consumed in each pass is relatively more important.

It is an object of this invention to provide catalysts for the oxidation of hydrocarbons to maleic anhydride which possess an acceptable selectivity as judged in the case of a "fuel lean" system by the pass yields obtainable with them under suitable conditions and in the case of a "fuel rich" system by the selectivities based on the hydrocarbon consumed at an acceptable conversion under suitable conditions.

The invention comprises novel catalysts for the production of maleic anhydride by the oxidation of hydrocarbons which catalysts comprise a phosphorus/vanadium mixed oxide promoted with tungsten, antimony, niobium and/or preferably molybdenum, the atomic ratio of vanadium to phosphorus being in the range 0.5 : 1 to 2 : 1 and the total atomic ratio of molybdenum, tungsten, antimony and/or niobium to vanadium being in the range 0.0025:1 to 1:1, the surface area of the catalyst being at least 10 m$^2$/g.

It is preferred that the atomic ratio of the total of tungsten antimony niobium and/or molybdenum to vanadium should be in the range 0.005:1 to 0.5:1. The atomic ratio of phosphorus to vanadium is preferably in the range 0.8:1 to 1.7:1.

It is desirable that the surface area of the catalyst should be as high as possible, preferably more than 15m$^2$/g for example in the range 20–50 m$^2$/g. Preferably the surface area does not exceed 150 m$^2$/g and more preferably it is at most 70 m$^2$/g.

Catalysts according to the invention may be made by precipitation of a phosphorus/vanadium mixed oxide complex from a suitable organic solvent optionally in the presence of water preferably in an amount of 1 to 5 gram molecules of water per gram atom of vanadium. The organic solvent may be an alcohol preferably having 3 to 6 carbon atoms, preferably a secondary alcohol for example isopropanol or isobutanol or an ether preferably a cyclic ether for example tetrahydrofuran.

The precipitation of the phosphorus/vanadium mixed oxide may be achieved by evaporating the organic solvent. The dry catalyst may be activated by heating it in the presence of a hydrocarbon for example n-butane. A solution of a vanadium compound in the solvent may be produced by mixing vanadium pentoxide, vanadium sesquioxide, a vanadyl halide, e.g. VOCl$_2$, a vanadium oxytrihalide, a vanadium oxydihalide, vanadyl sulphate, or vanadium (V) phosphate with the solvent. Preferably the precipitate is contacted during or after its formation with an acid stronger than phosphoric acid which is suitably hydrochloric, hydriodic, hydrobromic, sulphuric or nitric acid, before activation and preferably before removal of the organic solvent. Such acids may be formed in situ from anions present for example in the vanadium compound; for example sulphuric acid may be generated from vanadyl sulphate. Hydrochloric acid for example may be generated by hydrolysis of phosphorus oxytrihalides. Sulphuric acid is suitably present. Phosphorus may be added as orthophosphoric acid or its metal salts for example sodium dihydrogen phosphate; monofluoro phosphoric acid, phosphorus pentoxide, a phosphorus oxytrihalide or a condensed phosphorus acid, e.g. pyrophosphoric acid or tri poly phosphoric acid. If desired oxalic, formic, citric or other carboxylic acids may be added.

The tungsten, antimony, niobium and/or molybdenum may be added as a compound together with the vanadium and/or phosphoric acid or separately introduced into the solution or may be introduced by impregnating the precipitated dry or activated catalyst with a compound thereof in an aqueous solution or preferably in a solution in an organic solvent for example isobutanol. Suitable molybdenum compounds comprise molybdenum trioxide, dodecamolybdo-phosphoric acid, ammonium molybdate, molybdenum pentoxide, molydbenum dioxydichloride, and molybdenum pentahalides.

If it is desired to improve mechanical properties of the catalyst for example its resistance to attrition it may be treated with a suspension of an inert support for example alumina, titania, silicon carbide, Kieselguhr, pumice or preferably silica. Suitably a coloidal silica sol for example the material supplied under the trade name "LUDOX" by E I Du Pont de Nemours & Co is employed. The catalyst may be reinforced with such materials at any stage in its preparation. The surface area of the catalyst as quoted previously is however the surface area of the aforesaid catalyst material excluding any reinforcement or support. The surface area of the catalyst excluding the reinforcement or support may be determined directly when the catalyst is prepared first and the reinforcement or support is added subsequently. If the catalyst is formed on a reinforcement or support however the surface area of the catalyst according to this invention is defined as that which is possessed by a catalyst identically prepared but in the absence of the reinforcement or support.

It is preferred that catalysts according to this invention should comprise a B phase as disclosed in U.S. Pat. No. 3,864,280 preferably in an amount of at least 25% by weight and more preferably in excess of 50% by weight assessed as described therein.

The invention also comprises a process of oxidising a hydrocarbon as aforesaid to maleic anhydride by contacting it in the presence of oxygen with a catalyst as aforesaid. It is preferred to carry out the process using n-butane as the hydrocarbon and it is suitably fed in a concentration of 0.5-1.5% by volume in air to a fixed or fluidised bed of the catalyst. The oxidation is preferably carried out at a temperature in the range 250°-600° C. and more preferably 300°-400° C. The reaction may be carried out at a pressure of 0.5 to 20 atmospheres absolute and is more preferably carried out at a pressure in the range 1-3 atmospheres.

EXAMPLE 1 (Comparative)

Vanadium pentoxide (182 g) was suspended in isobutanol (100 mls) and hydrogen chloride gas was passed through the suspension whilst maintaining the temperature at about 30° C. until the vanadium pentoxide dissolved to give a dark brown solution. To this solution phosphoric acid (100%, 236 g) dissolved in isobutanol (240 ml) was added and the resulting solution was refluxed for about 2 hours and at this stage a dark blue solution had been obtained. Part of the solvent was then removed by distillation and the resulting blue precipitate was filtered and washed with a little isobutanol, and then dried in air at 150° C. The P : V atomic ratio of this catalyst precursor is 1.2:1. A portion of the dried solid was mixed with pelleting agent sold under the trade name "Sterotex" (2% by wt) and pelletized under a pressure of 17 tons. The pellet was then crushed and sieved to give particles 500-710 in size and a 5.0 mls portion was charged to a tubular fixed bed reactor. The catalyst was then calcined in situ by heating to 385° C. at a rate of 3° C./min whilst 1.5% n-butane by volume in air was flowed through the bed at a Gas Hourly Space Velocity (GHSV) of 1000 hrs$^{-1}$. After calcination at a reactor temperature of 340° C., atmospheric pressure and a GHSV of 205 hrs$^{-1}$ of the above gas mixture the catalyst gave 52% molar pass yield of maleic anhydride at a butane conversion of 65%. The surface area of the final catalyst was 14 m$^2$/g.

EXAMPLE 2

Vanadium pentoxide (91 g) and molybdenum trioxide (4.32 g) were suspended in isobutanol (500 mls) and hydrogen chloride gas was passed through the suspension whilst maintaining the temperature at about 30° C. until the solids dissolved to give a dark brown solution. To this solution phosphoric acid (100%, 118 g) dissolved in isobutanol (120 mls) was added and the resulting solution was refluxed for about 2 hours and at this stage a dark blue solution had been obtained. Part of the solvent was removed by side arm distillation and the resulting green blue precipitate was collected by filtration and washed with a little isobutanol, and then dried at 150° C. in air. The P:V: Mo atomic ratios of this precursor was 1.2:1.0:0.04. A portion of the dried solid was mixed with 2% by weight of a pelleting agent sold under the trade name "Sterotex" and pelletized to 17 tons. The pellet was then crushed and sieved to yield particles having a size range of 500-710 and a 5.0 ml portion was charged to a tubular fixed bed reactor. The catalyst was then calcined in situ by the procedure detailed in the comparison example. After calcination, at a reactor temperature of 340° C. and a GHSV of 300 hrs$^{-1}$ of 1.5% n-butane by volume in air at atmospheric pressure the catalyst gave a molar pass yield in excess of 70% at a butane conversion of 85%. The surface area of the final catalyst was 24 m$^2$/g.

EXAMPLE 3

Vanadium pentoxide (91 g) and molybdenum trioxide (5.9 g) were suspended in isobutanol and hydrogen chloride gas was passed through the suspension whilst maintaining the temperature at about 30° C. until the solids dissolved to give a dark brown solution. To this solution phosphoric acid (100%, 118 g) dissolved in isobutanol (120 mls) was added and the resulting solution was refluxed for 2 hours and at this stage a dark blue solution had been obtained. The solvent was removed by side arm distillation and the resulting blue solid was dried at 150° C. in air. The P:V:Mo ratio of the catalyst precursor was 1.2: 1;0 : 0.037. A portion of the dried solid was mixed with a pelleting agent sold under the trade name "Sterotex" (2% by wt) and pelletized at a pressure of 17 tons. The pellet was then crushed and sieved to yield particles having a size range of 500 to 710 and a 5.0 ml portion was charged to a fixed bed reactor. The catalyst was then calcined in situ as detailed in the previous Examples. After calcination, at a reactor temperature of 340° C. and a GHSV of 148 hrs$^{-1}$ of 1.5% by volume n-butane in air at atmospheric pressure the catalyst gave a molar pass yield in excess of 68% at a n-butane conversion of 92%. The surface area of the final catalyst was 18 m$^2$/g.

EXAMPLE 4

Vanadium pentoxide (91 g) and niobium pentoxide (9.3 g) was suspended in isobutanol (500 mls) and hydrogen chloride gas was passed through the suspension whilst maintaining the temperature at about 30° C. until the solids dissolved to give a dark brown solution. To this solution phosphoric acid (100%, 118 g) dissolved in isobutanol (120 mls) was added and the resulting solution was refluxed for about 2 hours and at this stage a dark blue solution had been obtained. Part of the solvent was removed by side arm distillation and the resulting blue precipitate was collected by filtration and washed with a little isobutanol, and then dried at 100° C. in air. The P:V:Nb atomic ratio of this precursor was 1.2:1.0:0.07. A portion of the dried solid was mixed with 3.0% by weight of a pelleting agent sold under the trade name "Sterotex" and pelletized at a pressure of 17 tons. The pellet was then crushed and sieved to yield particles 500-710 size range and a 5.0 ml portion was charged to a tubular fixed bed reactor. The catalyst was then calcined in situ by the procedure detailed in Example 1. After calcination, at a reactor temperature of 340° C. and a GHSV of 100 hr$^{-1}$ of 1.5% by volume of n-butane in air at atmospheric pressure the catalyst gave 70% molar pass yield of maleic anhdyride at a butane conversion of 96%. The surface area of the final catalyst was 15 m²/g.

EXAMPLE 5

Vanadium pentoxide (91 g) and antimony trichloride (34.2 g) was suspended in isobutanol (600 mls) and hydrogen chloride gas was passed through the suspension whilst maintaining the temperature at about 30° C. until the solids dissolved. To this solution phosphoric acid (100%, 118 g) dissolved in isobutanol (120 mls) was added and the resulting brown solution was refluxed for about 3 hours. At this stage a dark blue solution had been obtained. Part of the solvent was removed by side arm distillation and the resulting blue precipitate was collected by filtration and washed with a little isobutanol. The P:V:Sb atomic ratio of the precursor was 1.2:1.0:0.08. A portion of the dried solid was mixed with 3.0% by weight of a pelleting agent sold under the trade name "Sterotex" and pelletized under a pressure of 17 tons. The pellet was then crushed and sieved to give particles 500–710 in size and a 5.0 ml portion was charged to a fixed bed reactor. The catalyst was then calcined in situ by the procedure detailed in Example 1. After calcination, at a reactor temperature of 385° C. and GHSV of 205 hr$^{-1}$ of 1.5% by volume n-butane in air, at atmospheric pressure the catalyst gave a molar pass yield of maleic anhydride in excess of 61% at a n-butane conversion of 93%. The surface area of the final catalyst was 14 m²/g.

EXAMPLE 6

A catalyst precursor was prepared as described in Example 1 with a P:V atomic ratio of 1.2:1. Molybdenum trioxide (0.88 g) was thoroughly mixed by grinding with a portion of the catalyst precursor (25 g) to give a P:V:Mo atomic ratio of 1.2:1.0:0.05. A portion of this solid was mixed with pelleting agent sold under the trade name "Sterotex" (3% by weight) and pelletized to a pressure of 17 tons. The pellet was then crushed and sieved to give particles 500–710 in size and a 5.0 ml portion was charged to a tubular fixed bed reactor. The catalyst was then calcined in situ by the procedure detailed in example 1. After calcination at a reactor temperature of 340° C. and GHSV of 200 hr$^{-1}$ of 1.5% by volume of n-butane in air at atmospheric pressure the catalyst gave 69% molar pass yield of maleic anhydride at a butane conversion of 93%. The surface area of the final catalyst was 17 m²/g.

EXAMPLE 7

A catalyst precursor was prepared as stated in Example 1 and a portion of the solid was mixed with pelleting agent sold under the trade name "Sterotex" (3% by weight) and was pelletized to a pressure of 17 tons. The pellet was then crushed and sieved to give particles 500–710 in size. The particles were then impregnated with a solution of dodeca molybdophosphoric acid in isobutanol (10.2 g/100 mls) to give a catalyst precursor with a Mo:V atomic ratio of 0.04:1. After drying at 120° C. in air a 5.0 ml portion was charged to the tubular fixed bed reactor and the catalyst was calcined in situ as stated in Example 1. After calcination the catalyst gave a 61% molar pass yield of maleic anhydride at a butane conversion of 84.4% of a reactor temperature of 340° C. and a GHSV of 200 hr$^{-1}$ of 1.5% n-butane in air at atmospheric pressure.

EXAMPLE 8

A series of catalyst precursors were prepared with varying V:P:Mo atomic ratios according to the method stated in Example 2 except that the following quantities of molybdenum trioxide was used: 3.7 g (V:Mo=1.0:026), 4.32 g (V:Mo=1:0.04) and 9 g (V:Mo=1:0.076). The catalyst precursors were pelletized, sieved, loaded to the tubular fixed bed reactor and calcined in situ by the procedure detailed in Example 1. A mixture of 1.5% n-butane in air at atmospheric pressure was then passed through the catalysts at 385° C. and the yields of maleic anhydride were determined. The results are given in Table 1:

TABLE 1

| Atomic Ratio P/V/Mo | G.H.S.V. (hr$^{-1}$) | Maleic Anhydride Molar Pass Yield % | n-butane Conversion % | Surface Area m²/g. |
|---|---|---|---|---|
| Comparative 1.2/1/0 | 750 | 50 | 74.2 | 14 |
| 1.2/1/0.026 | 726 | 60 | 90 | 22 |
| 1.2/1/0.04 | 750 | 66 | 98 | 24 |
| 1.2/1/0.076 | 416 | 65 | 95 | 16 |

We claim:

1. A catalyst for the production of maleic anhydride by the oxidation of a hydrocarbon, which comprises a phosphorus/vanadium mixed oxide with at least one promoter selected from the group consisting of tungsten, antimony, niobium, and molybdenum, the atomic ratio of vanadium to phosphorus being in the range 0.5:1 to 2:1 and the total atomic ratio of molybdenum, tungsten, antimony or niobium to vanadium being in the range 0.025:1 to 1:1, the surface area of the catalyst being at least 10 m²/g, wherein said catalyst comprises a phase having a characteristic powder x-ray diffraction pattern using copper Kα-radiation as follows:

| | Line position | |
|---|---|---|
| d (Angstrom | 2.0 degrees | Intensity, I |
| 6.3 | 14.2 | 10 |
| 4.8 | 18.5 | 7 |
| 3.9 | 23.0 | 100 |
| 3.13 | 28.5 | 58 |
| 2.98 | 30.0 | 29 |
| 2.65 | 33.8 | 7 |

2. A catalyst as claimed in claim 1 in which the surface area is in the range 20–50 M²/g.

3. A process for the production of a catalyst as claimed in claim 1 which comprises precipitating the phosphorus/vanadium mixed oxide complex from an organic solvent in which W, Sb, Nb and Mo is present.

4. A process as claimed in claim 3 in which the precipitate is contacted during or after its formation with an acid stronger than phosphoric acid before separation of the organic solvent.

5. A process as claimed in claim 3 in which the tungsten, antimony, niobium and molybdenum is present in solution in the organic solvent.

6. A process as claimed in claim 3 in which the mechanical properties of the catalyst are improved by treating it with a suspension of an inert support.

* * * * *